United States Patent [19]

Tucchio

[11] Patent Number: 5,448,918
[45] Date of Patent: Sep. 12, 1995

[54] BIAXIAL COMPRESSION TESTING DEVICE

[75] Inventor: Michael A. Tucchio, East Lyme, Conn.

[73] Assignee: The United States of America as represented by the Secretary of the Navy, Washington, D.C.

[21] Appl. No.: 298,910

[22] Filed: Aug. 31, 1994

[51] Int. Cl.⁶ .......................... G01N 3/32; G01N 3/08
[52] U.S. Cl. .......................................... 73/819; 73/818; 73/856
[58] Field of Search ................. 73/818, 819, 825, 856, 73/857, 821, 822, 823, 824

[56] References Cited

U.S. PATENT DOCUMENTS

| 4,552,024 | 11/1985 | Baver et al. | 73/821 |
| 5,063,785 | 11/1991 | Labuz et al. | 73/821 |

FOREIGN PATENT DOCUMENTS

| 638871 | 12/1978 | U.S.S.R. | 73/856 |
| 924542 | 4/1982 | U.S.S.R. | 73/824 |
| 1163197 | 6/1985 | U.S.S.R. | 73/825 |
| 2611904 | 9/1988 | U.S.S.R. | 73/825 |
| 1439460 | 11/1988 | U.S.S.R. | 73/856 |
| 1613926 | 12/1990 | U.S.S.R. | 73/856 |

Primary Examiner—Richard Chilcot
Assistant Examiner—George M. Dombroske
Attorney, Agent, or Firm—Michael J. McGowan; James M. Kasischke; Prithvi C. Lall

[57] ABSTRACT

A biaxial compression testing device formed by two modified beams joined together to form an X-shape with the support structure, such as webs and upper flanges, removed in the region of the X intersection, thereby leaving a rectangular opening. The rectangular opening has dimensions slightly greater than the widths of the beams and is open from the upper surfaces downward to the lower surfaces which are joined together forming an X-configuration. This configuration has a flexing characteristic in the direction perpendicular to the plane of the joined beams. A test specimen support plate is attached to the underside of one of the upper surfaces and is located so as to slide below the opposing upper surface during flexing of the x-beam assembly. Each beam is supported by a roller pin. Additional roller pins are located on the specimen support plate between each beam upper flange and a specimen to be tested. These roller pins prevent any torsional load from reaching the test specimen. The single actuating force is applied to cause the X-beams to flex into a concave shape thereby applying a part of the actuating force axially along each beam. The configuration provides a force transfer assembly which is actuated by a single load force, but provides a biaxial load on the test specimen.

13 Claims, 7 Drawing Sheets

BIAXIAL COMPRESSION TESTING DEVICE

STATEMENT OF GOVERNMENT INTEREST

The invention described herein may be manufactured and used by or for the Government of the United States of America for Governmental purposes without the payment of any royalties thereon or therefor.

BACKGROUND OF THE INVENTION

1. Technical Field of the Invention

The invention relates generally to compression testing machines and more particularly to machines applying biaxial compression loads.

2. Description of the Prior Art

There are many types of biaxial compression testing devices available in the prior art. Typically, these devices use two force actuators for applying a biaxial load to a test specimen.

Actuators used include hydraulic pistons and jacks, mechanically and electrically operated screws and the like. In order to produce accurate loading of a test specimen in two directions, relatively complicated testing machines are required. In particular, it is necessary to avoid tangential and torsional loads on the test sample while simultaneously applying specific loads to the test sample in two directions. When it is desired to apply a specific ratio between forces in the two applied directions over a range of load forces, complex hydraulic pressure control or piston sizing is required in testing machines having dual actuators. Likewise, in the jack or screw type machines, the use of dual actuators requires a relatively complicated means of controlling the differential action necessary to produce a specific ratio between the biaxial loads.

SUMMARY OF THE INVENTION

It is an object of the present invention to provide a compression testing device adapted to apply biaxial compressive loads to a test specimen using a single input force.

It is another object of the invention to provide a biaxial compression testing device having an adjustment means whereby the ratio of forces applied along axes can be varied.

It is yet another object of the invention to provide a biaxial compression testing device having a means to prevent the transmission of torsional loads to a test specimen.

In accordance with these and other objects, a biaxial compression testing device formed with two modified beams is provided. The beams are joined together to form an X shape and are modified to remove support structure such as the webs and upper flanges in the region of the X intersection, thereby leaving a rectangular opening. The rectangular opening has dimensions slightly greater than the widths of the beams and is open from the upper surface downward to the lower surface. The lower surfaces are joined together, thereby providing a fixed X-configuration having a flexing characteristic in a direction perpendicular to the plane formed by the joined beams. A specimen support plate is welded to the underside of one of the upper surfaces and is free to slide under the opposing upper surface. The entire X structure formed by the beams is supported on four lower roller pins, one pin under each end of the beams. Four upper roller bearings are placed at the cut-off ends of the upper flange and rest on the specimen support plate. These upper roller bearings eliminate any bending or torsional loads on the test specimen. The test specimen is placed between the upper roller bearings and a single load device is used to apply a downward force on the upper flanges of the X-configured beams. The test fixture formed by the beams lower surface flexes under the download to cause a biaxial compression at the beam intersection. Relocation of the lower roller pins change the ratio of the biaxial loads applied to the test specimen.

BRIEF DESCRIPTION OF THE DRAWINGS

The foregoing objects and other advantages of the present invention will be more fully understood from the following detailed description and reference to the appended drawings wherein.

DESCRIPTION OF THE PREFERRED EMBODIMENTS

Figure 1:
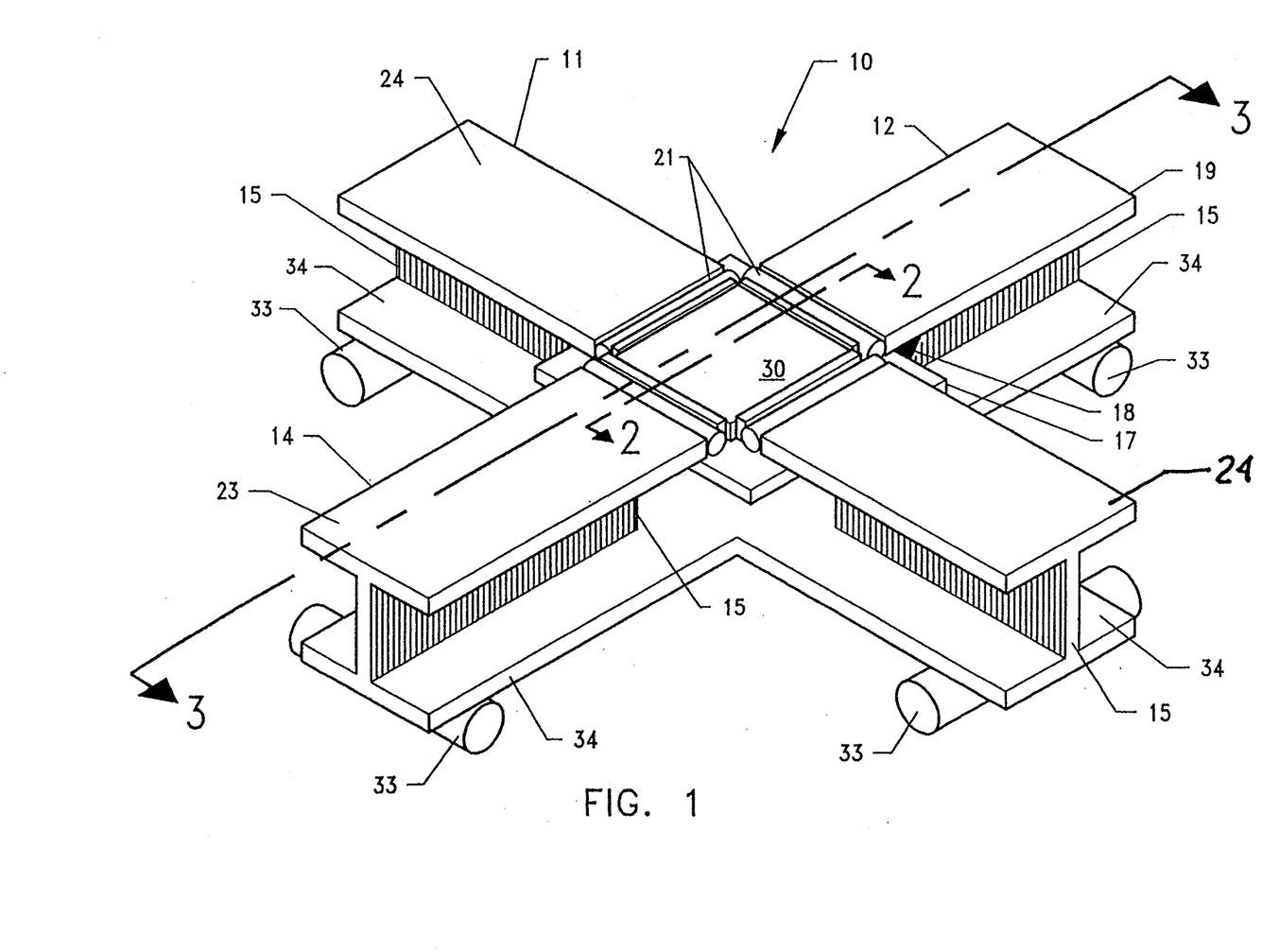
FIG. 1 is a perspective view of the biaxial testing device with the anvil removed.

Referring now to FIG. 1, the biaxial compression testing device, designated generally by the reference numeral 10, is shown with its major components. The device (shown without the anvil, for clarity) comprises first and second beams, 11 and 12, welded together at the intermediate region thereof at right angles to form a X-configured test fixture having four rigid beam segments. The lower flanges 34 are supported by lower roller pins 33. The upper flange 14 and web 15 are removed from each beam at the frame intersection. Beams 11 and 12 can be any substantially rigid beams such as I-beams (shown), box girders, or solid stock having flat upper and lower surfaces. A plate 17, to provide support for a specimen 30 is welded (weld 18) under a first upper flange 19 but is free to slide under the opposing flange 23. Likewise, the flanges 24 on either side of the specimen support plate 17 slide over the plate 17 during testing. This sliding action allows compression movement of the flange ends during the loading process with no axial restraint caused by the specimen support plate 17. Specimen 30 is placed in the opening between the upper flanges 19, 23 and 24 and is held in position by specimen support plate 17. Upper roller bearings 21 are positioned between the flange ends and specimen 30 to prevent the transmission of bending loads to specimen 30 while allowing axial (linear) loads to be applied to the specimen. Roller bearings 21 are equal in diameter to the thickness of specimen 30 and are made of hardened steel. These bearings 21 are placed next to the upper flanges as shown. Sections 2—2 and 3—3 show the orientation of the sectional views provided in FIGS. 2 and 3, respectively.

Figure 2:
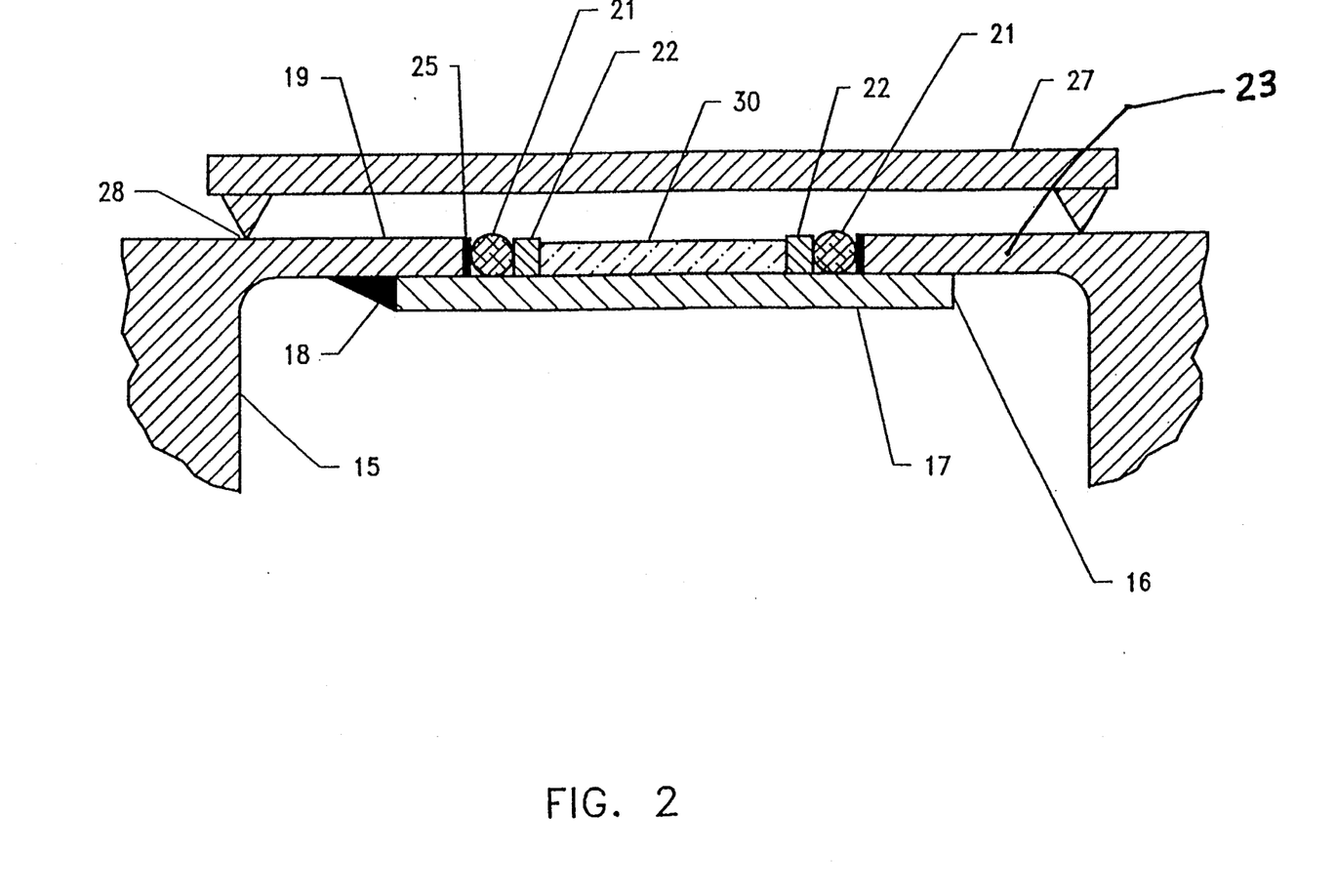
FIG. 2 is a sectional view of the compression section taken along section line 2—2 of FIG. 1 showing a test sample.

Additional details of the load application to the specimen 30 can be seen in FIG. 2. The specimen 30 is supported by specimen support plate 17. The support plate is welded, depicted by weld 18, to one of the cut-off upper flanges. The opposite end 16 of support plate 17 is not attached to the adjacent upper flange 23 and is free to slide in and out as a load is applied. Upper roller bearings 21 are located adjacent to the cut-off inner ends of the upper flanges, flange 19 having the weld, flange 23 opposite the welded flange, and the flanges 24 on the sides. A load plate 22 is placed between force application bearings 21, preferably roller bearings, and each end of the test specimen 30. These load plates 22, which are slightly larger than the specimen 30 are placed in contact with the specimen 30. Shims 25 can also be installed so that the assembly is snug within the upper flanges 19, 23, and 24 of the test fixture. An anvil 27 is used to apply a load to the test fixture with the points of load application 28 being applied approximately over the location of each cut-off web 15. Anvil 27 thus has four points of load application 28, positioned on each upper flange approximately over its web 15.

Figure 3:
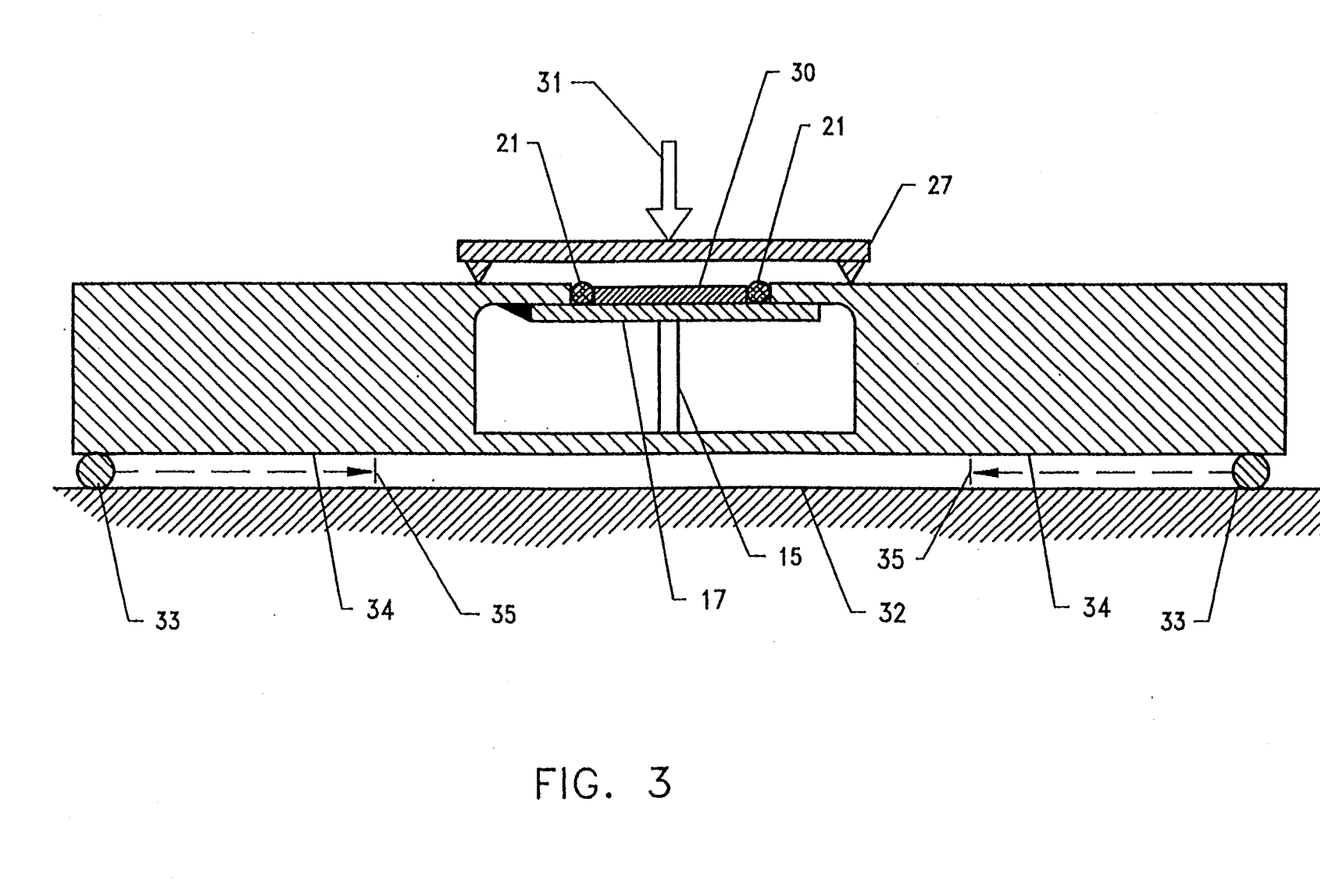
FIG. 3 is a sectional view of the complete assembly of the biaxial testing device taken along section 3—3 of FIG. 1.

Referring now to FIG. 3, the entire assembly is placed under the load application device 31 on an appropriate loading table 32. Lower roller pins 33 support the test fixture above load table 32. The loading device 31 exerts a single force on anvil 27. As the beams of the test fixture flex to an upwardly concave configuration, the single downward load is converted in two distinct biaxial horizontal loads. Two lower roller pins 33 are shown in this figure, however as may be noted in FIG. 1, each leg of the test fixture is supported by a single lower roller pin 33. The distance between roller pins 33 under the bottom flanges 34 can be varied from one leg of the frame to the other to obtain the desired ratio of biaxial loading. By moving one set of pins 33 inward to a point 35 under the point of load application, that is, approximately under the location of the cut-off webs, the forces on the test specimen in one direction can be reduced to zero, thereby providing a uniaxial compression testing configuration. Similarly, any desired ratio between the forces in a biaxial test can be easily set up by moving one or the other sets of lower roller pins 33. Changing the location of the pins 33 provides a unique feature wherein the application of a single force to the test fixture can produce any desired ratio of forces applied biaxially to the test specimen. This ratio will remain constant as the single force is varied over a desired test range.

Figure 4:
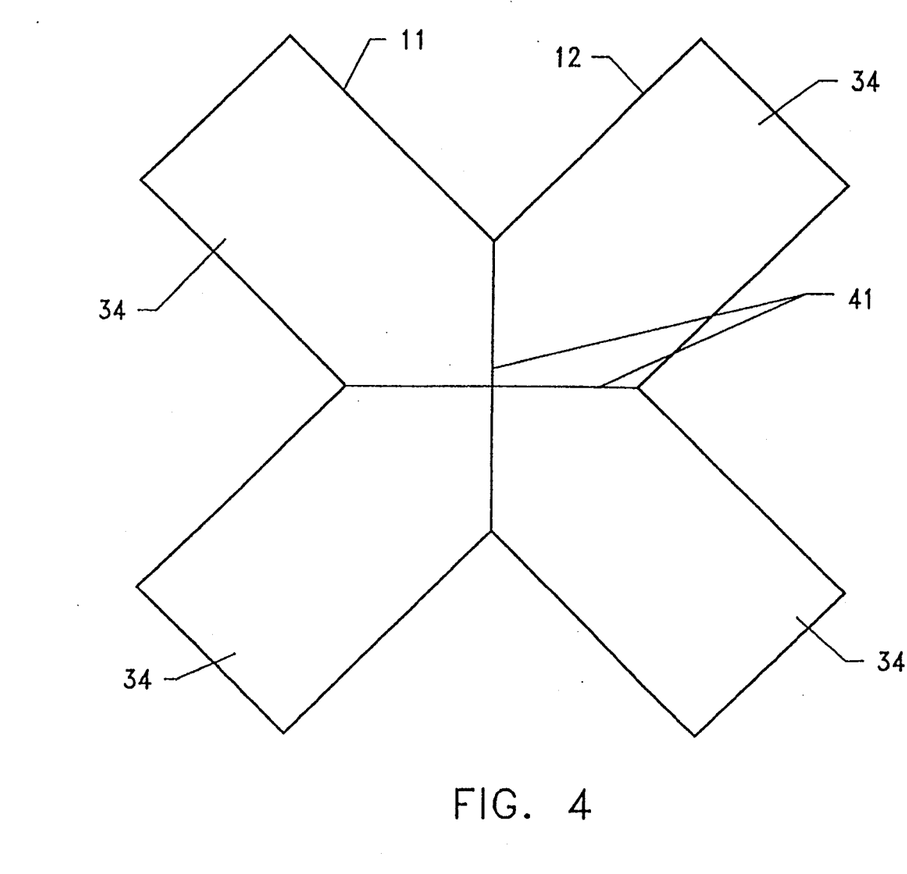
FIG. 4 is a bottom view showing the lower flange welds.

FIG. 4 provides a bottom view of the X-configuration offered by beam 11 and beam 12. The lower flanges 34 are visible at the intersection of the two beams 11, 12 and these flanges 34 are joined by welds 41 running along diagonal cuts. This weld results in a consistent flexibility of test structure 10 along both beams 11 and 12.

Figure 5:
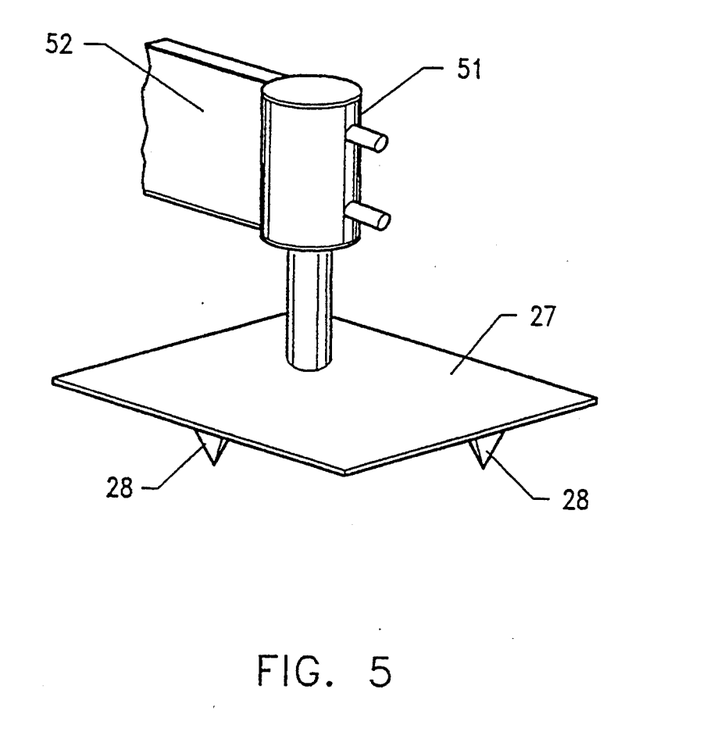
FIG. 5 is a side view of the hydraulic actuator assembly.
Figure 6:
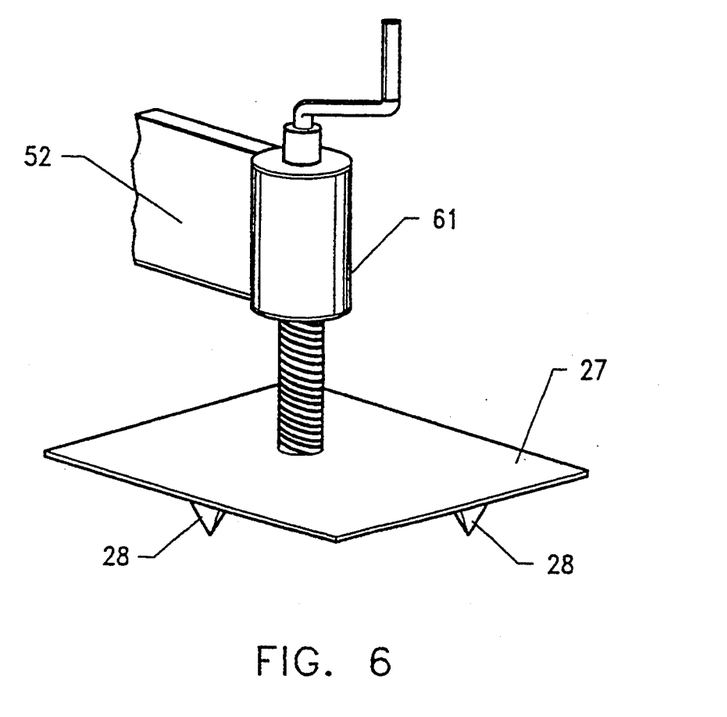
FIG. 6 is a side view of the screw jack actuator assembly.

FIGS. 5 and 6 depict typical force application devices which provide the single vertical force necessary to operate the invention. In FIG. 5, a hydraulic actuator 51 grounded to structure 52 is used to apply the desired force to anvil 27 having load application points 28. Actuator 51 acts as load application device 31. Another load application device is the screw jack 61 grounded to structure 52 as shown in FIG. 6. Other devices including electrically driven jack, levers, or the like can be substituted for device 31 within the scope of the invention.

Figure 7:
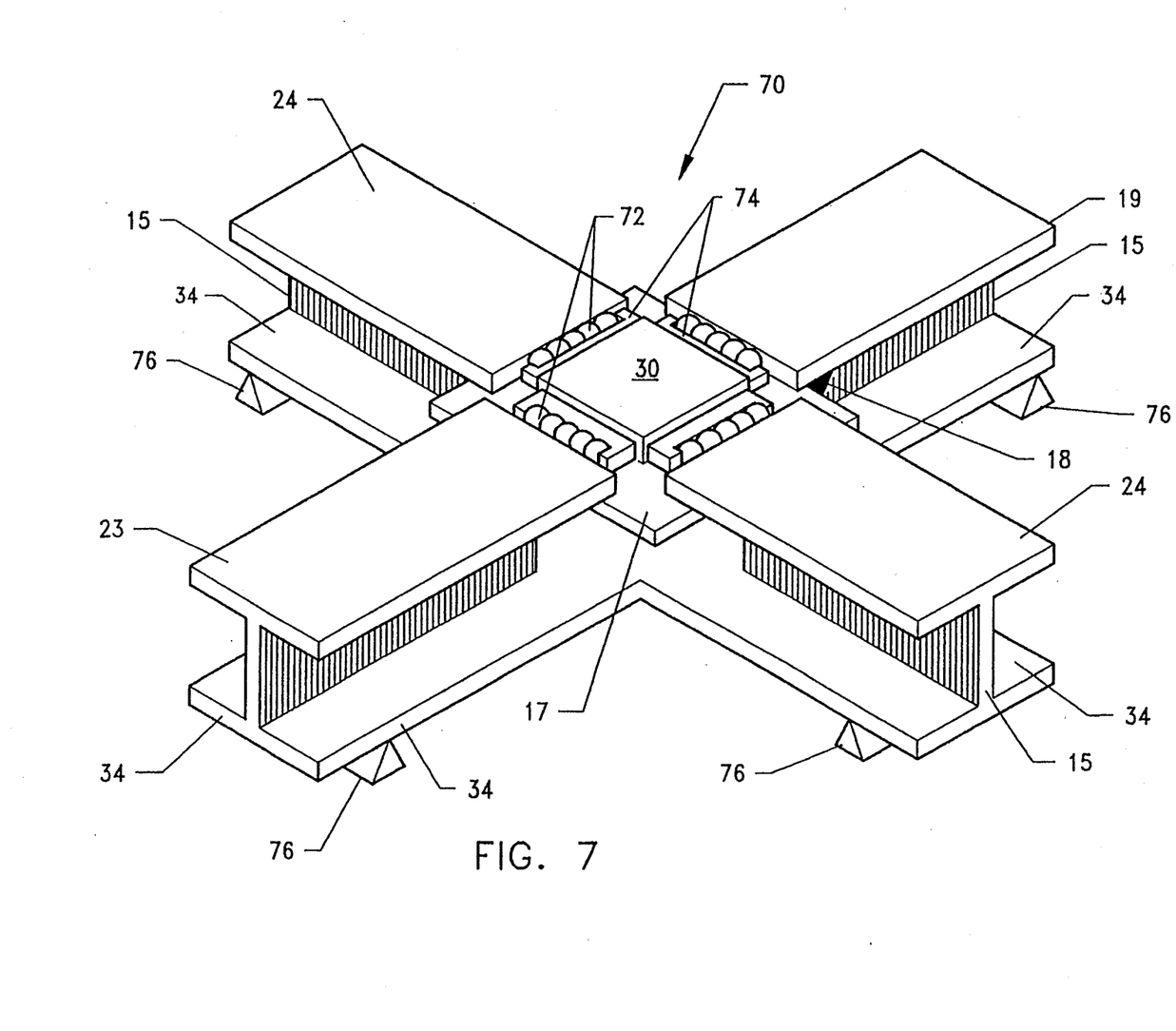
FIG. 7 is a perspective view of an alternate embodiment of the biaxial testing device with the anvil removed.

In FIG. 7 there is shown an alternate embodiment 70 of the biaxial compression test device of the current invention. This embodiment uses ball bearings 72 in place of roller bearings 21. A plurality of ball bearings 72 allows compression of specimen 30 without creating shear forces parallel to roller bearings 21. Alternate embodiment 70 is further provided with load plates 74 having end pieces for containing ball bearings 72. This embodiment is useful when specimen 30 undergoes a large amount of contraction during the test. This embodiment of the test device also uses support prisms 76 in place of the roller pins 33 of the first embodiment. Support prisms 76 allow pivoting of the supported beam while not permitting motion in a lateral direction.

Figure 8:
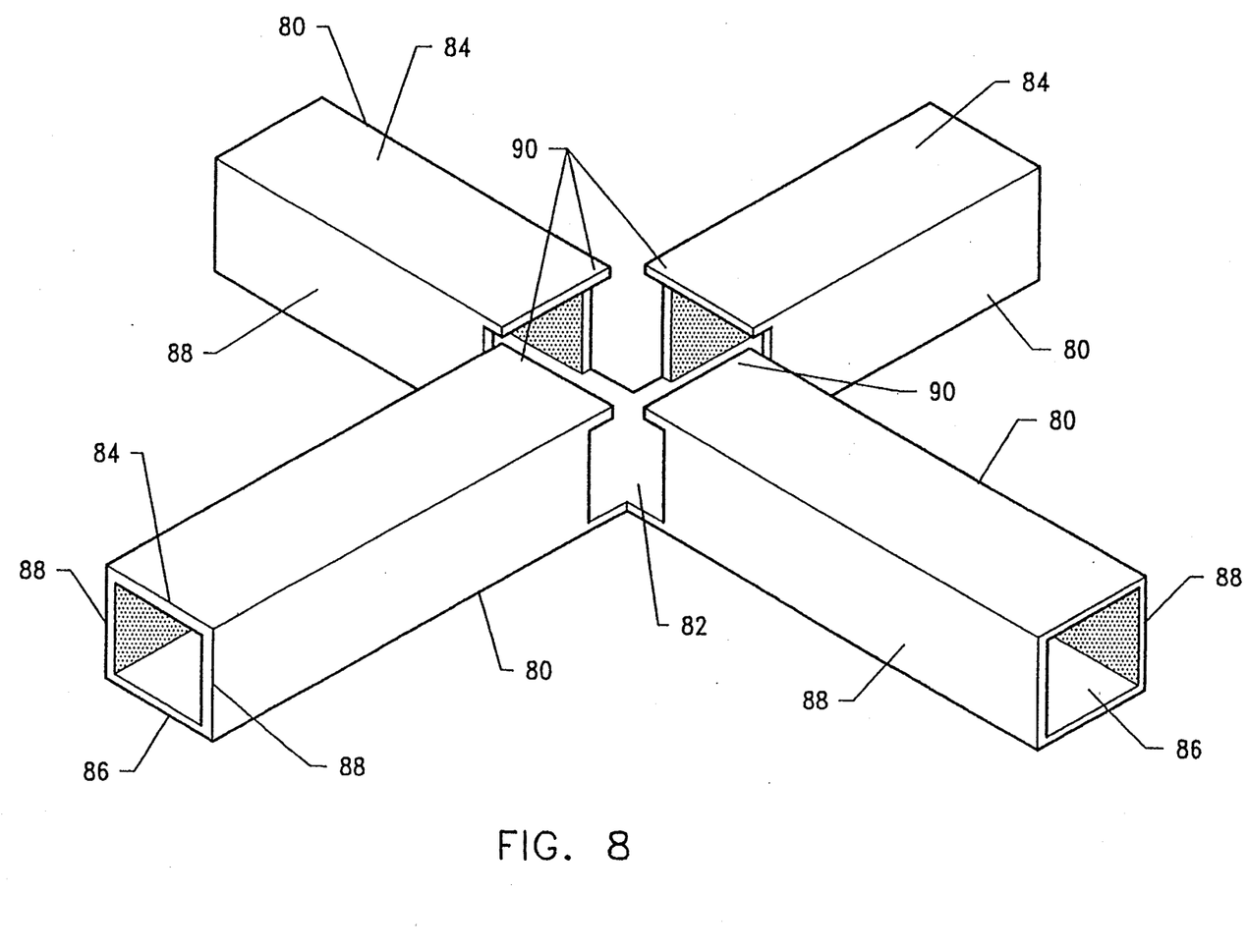
FIG. 8 is a perspective view of an alternate embodiment of the biaxial testing device constructed with box girders.

In FIG. 8 there is shown a force transfer assembly in accordance with an alternate embodiment of the current invention. For clarity in showing all aspects of this embodiment, the anvil, bearings, support plate and lower roller pins have been removed. Four rigid beam segments 80 are shown joined at right angles to each other to a bending plate 82. A gap is defined above bending plate 82. Beam segments 80 are made from box girder having an upper plate 84, a lower plate 86, and side plates 88. A force application flange 90 extends into the gap from the upper plate of each segment 80.

The advantages and new features of the present invention are numerous. The upper bearing and shim arrangement avoid the transmission of tangential and bending loads to the test specimen. A single force actuator applies a biaxial load to the specimen. The ratio of forces in the two directions may be adjusted by the simple operation of positioning the lower roller pins and will remain adjusted at the selected ratio over a wide range of load applications.

It will be understood that many additional changes in the details, materials, steps and arrangement of parts, which have been herein described and illustrated in order to explain the nature of the invention, may be made by those skilled in the art within the principle and scope of the invention as expressed in the appended claims. Although the current embodiment shows an assembly made from beams, it is apparent that any substantially rigid stock such as box girders, solid square stock of the like can be used for this device. Likewise, any of the bearings shown herein can be replaced with mechanically equivalent bearings known in the art.

What is claimed is:

1. A biaxial compression testing device comprising:
   force transfer assembly having four rigid beam segments joined together at modified ends, said ends forming a bending plate at the intersection thereof, each said beam segment having a force application member on the upper surface thereof, said beam segments being joined together at right angles to each other, and said force application members defining a gap therebetween above said bending plate;
   a specimen support plate attached to one said force application member of said force transfer assembly and extending from said force application member into said gap;
   a support means located beneath and supporting each said beam segment at a linear contact region in a horizontal plane perpendicular to the length of said beam segment to allow fulcral rotation of said beam segment around said linear contact region, and each said support means being positionable along said beam segment;

an anvil positioned on top of said beam segments above said gap to transmit force evenly through said anvil to said force transfer assembly on each side of said gap; and a force actuating means attached to said anvil to provide a force to said anvil, said force being transmitted to said force transfer assembly and generating a moment between said force applied to said anvil and said support means causing bending of said bending plate and reducing the space between said force application members.

2. The apparatus of claim 1 further comprising a plurality of force application bearings supported by said specimen support plate and in contact with said force application members.

3. The apparatus of claim 2 wherein said force application bearings are roller bearings having an axis parallel to the region of contact with said force application members.

4. The apparatus of claim 1 wherein said force actuating means is a screw jack.

5. The apparatus of claim 1 wherein said force actuating means is a hydraulic jack.

6. The apparatus of claim 2 wherein said force application bearings comprise a plurality of ball bearings contained by said force application members and said specimen support plate.

7. The apparatus of claim 6 wherein said force actuating means is a screw jack.

8. The apparatus of claim 6 wherein said force actuating means is a hydraulic jack.

9. The apparatus of claim 2 wherein said beam segments are I beams having the upper flange and web portion removed from said beam segments at one end, said bending plate being formed by the lower flanges of each said beam segment joined together at said one end, and said force application members being formed from the upper flange of each said beam segment.

10. The apparatus of claim 2 wherein said beam segments are box girders having an upper plate and side plates removed from said beam segments at one end, said bending plate being formed by the lower plate of each said beam segment joined together at said one end, and said force application members being formed from the upper plate of each said beam segment.

11. A biaxial compression testing device comprising:

an I-beam assembly having four I-beam segments, each segment having an upper and lower flange connected by a web, attached together in an X-configuration and further having a section of web and upper flange removed from said I-beam segments at the attachment location;

a specimen support plate attached to an upper flange of said I-beam assembly at said attachment location;

a first and second pair of bearings supported by said specimen support plate and in contact with upper flanges;

a plurality of shims placed between each bearings and the adjacent upper flange;

a first and second pair of roller pins located beneath and supporting said I-beam assembly each roller pin supporting one I-beam segment;

an anvil contacting and applying transmitting actuating force to the upper flanges of said I-beam assembly; and a force actuator connected to said anvil and applying actuating force thereto.

12. A biaxial compression testing device as in claim 11 wherein said force actuator is a hydraulic actuator.

13. A biaxial compression testing device as in claim 11 wherein said force actuator is a screw jack.

* * * * *